United States Patent
Sartor et al.

(10) Patent No.: US 8,426,597 B2
(45) Date of Patent: Apr. 23, 2013

(54) NITRATE DERIVATIVES OF CILOSTAZOL FOR THE TREATMENT OF VASCULAR AND METABOLIC DISEASES

(75) Inventors: Dirk Sartor, Rimbach (DE); Armin Scherhag, Dornach (CH)

(73) Assignee: Cardiolynx AG, Basel (CH)

( * ) Notice: Subject to any disclaimer, the term of this patent is extended or adjusted under 35 U.S.C. 154(b) by 209 days.

(21) Appl. No.: 13/131,722

(22) PCT Filed: Dec. 1, 2009

(86) PCT No.: PCT/EP2009/066159
§ 371 (c)(1),
(2), (4) Date: May 27, 2011

(87) PCT Pub. No.: WO2010/063724
PCT Pub. Date: Jun. 10, 2010

(65) Prior Publication Data
US 2011/0230520 A1    Sep. 22, 2011

(30) Foreign Application Priority Data

Dec. 2, 2008  (EP) .................................. 08170435

(51) Int. Cl.
*C07D 215/38*      (2006.01)
(52) U.S. Cl.
USPC ........................................................ 546/158

(58) Field of Classification Search .................... 546/158
See application file for complete search history.

(56) References Cited

U.S. PATENT DOCUMENTS

| 4,277,479 A * | 7/1981 | Nishi et al. .................... 514/312 |
| 6,869,974 B1 | 3/2005 | Del Soldato |
| 2005/0261242 A1 | 11/2005 | Soldato |

FOREIGN PATENT DOCUMENTS

WO    00/61537    10/2000

OTHER PUBLICATIONS

Dirk Sartor et al., U.S. Appl. No. 13/641,747, entitled "Valsartan Derivatives Carrying Nitrogen Oxide Donors for the Treatment of Vascular and Metabolic Diseases", filed Oct. 17, 2012.
Dirk Sartor et al., U.S. Appl. No. 13/701,100, entitled "Nitrate and Diazeniumdiolate Derivatives of Pioglitazone", filed Nov. 30, 2012.
International Search Report issued Mar. 17, 2010 in International (PCT) Application No. PCT/EP2009/066159.
PCT Written Opinion of the International Searching Authority issued Mar. 17, 2010 in International (PCT) Application No. PCT/EP2009/066159.

* cited by examiner

*Primary Examiner* — D M Seaman
(74) *Attorney, Agent, or Firm* — Wenderoth, Lind & Ponack, L.L.P.

(57) ABSTRACT

Nitrate derivatives of cilostazol are described. They have superior properties and clinical advantages compared to cilostazol in the treatment of vascular and metabolic diseases.

14 Claims, No Drawings

NITRATE DERIVATIVES OF CILOSTAZOL FOR THE TREATMENT OF VASCULAR AND METABOLIC DISEASES

FIELD OF THE INVENTION

The invention relates to nitrate derivatives of cilostazol useful in the treatment of vascular and metabolic diseases.

BACKGROUND OF THE INVENTION

Vascular and metabolic diseases are, despite cancer, the leading causes of death in the western world. Although many different ways of treating vascular and metabolic diseases are known, there is still a need for improved medication. Lifestyle modifications and drug therapy can decrease and delay the morbidity and mortality associated with these diseases. Treatments which have been proven to reduce the risk for morbidity and mortality in vascular diseases have been typically shown to either improve impaired vascular function or to delay/prevent the progression of vascular dysfunction caused by hypertension, atherosclerosis or other classical metabolic risk factors. Examples for such treatments are calcium channel blockers, beta blockers, angiotensin-enzyme converting inhibitors or angiotension receptor blockers.

In patients with atherosclerosis, who are suffering e.g. from angina pectoris, one of the established standard treatments involves treatment with organic nitrates, specifically nitrate esters, such as glyceryl trinitrate (nitroglycerine), isosorbide dinitrate, or penta-erythrityl tetranitrate, which act all as coronary vasodilators and improve symptoms and exercise tolerance. Most organic nitrates (e.g. mononitrates and trinitrates) are fast acting pharmaceuticals with a relatively short halflife and have the typical disadvantage that patients develop a nitrate tolerance, meaning that part of the pharmacodynamic effect is lost during chronic treatment and a three times daily dosing regimen.

In the case of peripheral arterial disease (PAD) which is typically caused by hypertension and atherosclerosis and presents clinically with intermittent claudication, compounds with vasodilating properties have been shown to improve symptoms and walking. Two established licensed compounds for treatment of PAD patients are cilostazol (a phospho-diesterase III inhibitor) and pentoxifylline. Cilostazol (U.S. Pat. No. 4,277,479) acts as a direct arterial vasodilator. In addition to its reported vasodilator and antiplatelet effects, cilostazol has been proposed to have beneficial effects on plasma lipoproteins, increasing plasma high density lipoprotein cholesterol and apolipoproteins.

Nitrate esters of drugs in general are described in WO 00/61357. Diazeniumdiolate derivatives have recently been recognized as alternatives for nitrates, setting free two molecules of NO under physiological conditions. A diazeniumdiolate derivative of tacrine is described by L. Fang et al., J. Med. Chem. 51, 7666-7669 (2008).

SUMMARY OF THE INVENTION

The invention relates to compounds of formula 1

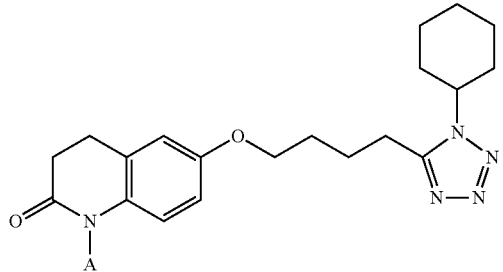

or the corresponding oxy-imine derivative

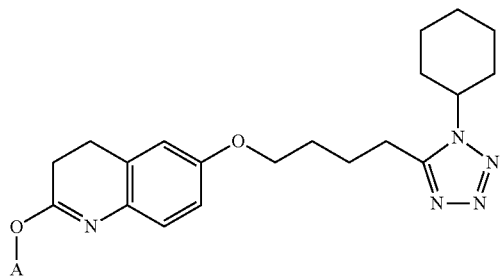

wherein A is
—(C=O)$_a$—(CH$_2$)$_b$—O—NO$_2$;
—(C=O)—(CH$_2$OCH$_2$)$_c$CH$_2$—O—NO$_2$;
—(CH$_2$CH$_2$O)$_c$CH$_2$CH$_2$—O—NO$_2$;
—(C=O)$_a$—(CH$_2$)$_d$—CH[(CH$_2$)$_e$—O—NO$_2$]$_2$;
—(C=O)—NR$^1$—(CH$_2$)$_b$—O—NO$_2$;
—(C=O)—O—(CH$_2$)$_b$—O—NO$_2$;
—CH$_2$O—(C=O)—NR$^1$—(CH$_2$)$_b$—O—NO$_2$; or
—CH$_2$O—(C=O)—O—(CH$_2$)$_b$—O—NO$_2$;
—CH$_2$O—(C=O)—(CH$_2$)$_b$—O—NO$_2$;
 a is 0 or 1;
 b is between 1 and 10;
 c is 1, 2 or 3;
 d is 0, 1 or 2;
 e is between 1 and 4;
 R$^1$ is H, C$_{1-4}$-alkyl or —CH$_2$O—(C=O)—NH—(CH$_2$)$_b$—O—NO$_2$; and such compounds wherein —O—NO$_2$ is replaced by

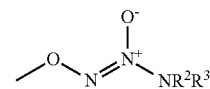

wherein R$^2$ and R$^3$ are both ethyl or 2-aminoethyl, or NR$^2$R$^3$ together represent pyrrolidine, piperidine, piperazine or 4-methylpiperazine.

Furthermore the invention relates to pharmaceutical compositions comprising the compounds as defined hereinbefore, to the compounds as defined hereinbefore for the treatment of vascular and metabolic diseases, and to a method of treatment of vascular and metabolic diseases using the compounds and pharmaceutical compositions as defined hereinbefore.

The compounds of the invention represent useful medicaments for the treatment of vascular and metabolic diseases, for example, atherosclerosis, in particular connected with hypertension, also ocular and pulmonary hypertension, heart failure, in particular chronic heart failure after a heart attack (myocardial infarction), stroke, angina pectoris, cerebrovascular disease, coronary artery disease, left ventricular dysfunction and hypertrophy, and peripheral arterial disease (PAD), in particular intermittent claudication. The compounds of the invention have superior vasodilating properties compared to cilostazol (formula 1, A=hydrogen).

DETAILED DESCRIPTION OF THE INVENTION

The compound of formula 1, wherein A is hydrogen, is known under the name cilostazol. The compound of formula 1A, wherein A is hydrogen, is a tautomeric form of cilostazol, wherein the amide function is present as an oxy-imine function (keto-enol tautomerisim). When, in a compound of formula 1A, A is different from hydrogen, the oxy-imine function cannot revert to the amide function and form a tautomeric equilibrium. Such a compound of formula 1A represents a stable regio-isomer of the corresponding compound of formula 1.

$C_{1-4}$-alkyl is methyl, ethyl, n-propyl, isopropyl, n-butyl, isobutyl, sec-butyl, or tert-butyl, preferably methyl, ethyl or n-propyl, in particular methyl.

The compounds of formula 1 and 1A, wherein A has the indicated meanings, are useful in the treatment of vascular and metabolic diseases.

Vascular diseases considered are, for example, hypertension and atherosclerosis and typical related consecutive diseases and their corresponding complications, in particular, ocular and pulmonary hypertension, chronic heart failure, heart failure after a heart attack (myocardial infarction), cerebral ischaemia in general and, specifically, transient ischaemic attacks (TIAs), prolonged neurological deficits (PRIND), stroke (ischaemic and non-ischaemic), chronic cerebrovascular diseases, stable and unstable angina pectoris, coronary artery disease, cardiac dysfunction, specifically left or right ventricular dysfunction and hypertrophy, peripheral arterial disease (PAD) at all stages, specifically including abnormalities in micro- and macrovascular function such as neuropathy, endothelial dysfunction, cold feet, impaired wound healing, ischaemic ulcers and necrosis, critical limb ischaemia, intermittent claudication, chronic or intermittent pain syndromes related to peripheral artery disease, polyneuropathy, and chronic and acute inflammatory vascular diseases. Furthermore, treatment and prophylaxis is considered of complications after peripheral vascular interventions such as balloon angioplasty and/or stenting, portal hypertension, chronic inflammatory vascular diseases, mixed connective tissue diseases with vascular complications, treatment of vascular complications in patients with Morbus Raynaud or Morbus Osler, treatment of typical micro- and macro-vascular complications of diabetes mellitus, abnormalities of platelet function such as increased platelet adhesion and resulting hypercoagulability, and conditions typically accompanying vascular diseases as described above.

Metabolic diseases considered are, for example, diabetes mellitus type 1 and 2, impaired glucose tolerance, all dyslipidaemias such hypercholesterolaemia, hypertriglyceridaemia, abnormalities of high density lipoproteins alone or in combinations with other dyslipidaemias, abnormalities of Apolipoprotein A1 or other subfractions of lipoproteins, and other metabolic diseases resulting in vascular complications and/or impaired platelet function.

Compounds of formula 1 and 1A can be manufactured by methods well known in the art. Preferably, cilostazol, i.e. the compound of formula 1, wherein A is hydrogen, is treated with an acylating compound or an alkylating compound, respectively, further carrying one or two bromine, chlorine or iodine atoms, according to standard procedures well known in the art. In the last step of the preferred synthesis, the bromine, chlorine or iodine is replaced by a nitrate ester or a diazeniumdiolate function by reaction with silver nitrate, or with a diazeniumdiolate in the presence of strong base in a dipolar aprotic solvent, respectively. In an alternative synthesis, the acylating or alkylating compound carries one or two hydroxy functions or protected hydroxy functions. These hydroxy groups are then transformed to a nitrate ester with nitric acid. A third synthesis procedure involves alkylation or acylation with the corresponding preformed reactive nitroxyalkyl or nitroxyacyl derivative, e.g. the 4-nitroxybutanoic acid pentafluorophenol ester. Introduction of a —CH$_2$O— (C=O)—NR$^1$—(CH$_2$)$_b$—O—NO$_2$ group can be performed directly with the corresponding highly reactive chloride, which at the same time produces the compound wherein A is —CH$_2$O—(C=O)—NR$^1$—(CH$_2$)$_b$—O—NO$_2$ and R$^1$ is a further —CH$_2$O—(C=O)—NH—(CH$_2$)$_b$—O—NO$_2$ group in the case that R$^1$ in the reactive chloride is hydrogen. Corresponding compounds with a —CH$_2$O—(C=O)—O—(CH$_2$)$_b$—O—NO$_2$ or —CH$_2$O—(C=O)—(CH$_2$)$_b$—O—NO$_2$ function are prepared analogously.

Preferred are compounds of formula 1, wherein

A is —(C=O)$_a$—(CH$_2$)$_b$—O—NO$_2$; —(C=O)—(CH$_2$OCH$_2$)$_c$CH$_2$—O—NO$_2$; —(CH$_2$CH$_2$O)$_b$CH$_2$CH$_2$—O—NO$_2$; or —(C=O)$_a$—(CH$_2$)$_d$—CH[(CH$_2$)$_e$—O—NO$_2$]$_2$; and a, b, c, d and e have the indicated meanings.

More preferred are compounds of formula 1, wherein

A is —(C=O)$_a$—(CH$_2$)$_b$—O—NO$_2$ or —(C=O)$_a$—(CH$_2$)$_d$—CH[(CH$_2$)$_e$—O—NO$_2$]$_2$; and a is 0 or 1; b is between 1 and 6; d is 0, 1 or 2; and e is 1 or 2.

Even more preferred are compounds of formula 1, wherein

A is —(C=O)$_a$—(CH$_2$)$_b$—O—NO$_2$ or —(C=O)$_a$—(CH$_2$)$_d$—CH[(CH$_2$)$_e$—O—NO$_2$]$_2$; and a is 1; b is 2, 3, 4 or 5; d is 0 or 1; and e is 1 or 2.

Even more preferred are compounds of formula 1, wherein

A is —(C=O)$_a$—(CH$_2$)$_d$—CH[(CH$_2$)$_e$—O—NO$_2$]$_2$; and a is 1; d is 0 or 1; and e is 1 or 2.

Further preferred are compounds of formula 1 or 1A, wherein

A is —(C=O)$_a$—(CH$_2$)$_b$—O—NO$_2$; —(C=O)$_a$—(CH$_2$)$_d$—CH[(CH$_2$)$_e$—O—NO$_2$]$_2$;

—(C=O)—NR$^1$—(CH$_2$)$_b$—O—NO$_2$; —(C=O)—O—(CH$_2$)$_b$—O—NO$_2$;

—CH$_2$O—(C=O)—NR$^1$—(CH$_2$)$_b$—O—NO$_2$; —CH$_2$O—(C=O)—O—(CH$_2$)$_b$—O—NO$_2$; or

—CH$_2$O—(C=O)—(CH$_2$)$_b$—O—NO$_2$;

a is 0 or 1; b is between 1 and 10; d is 0, 1 or 2; e is between 1 and 4;

R$^1$ is H, $C_{1-4}$-alkyl or —CH$_2$O—(C=O)—NH—(CH$_2$)$_b$—O—NO$_2$; and such compounds wherein —O—NO$_2$ is replaced by

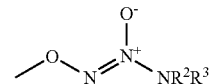

wherein R$^2$ and R$^3$ are both ethyl or 2-aminoethyl, or NR$^2$R$^3$ together represent pyrrolidine, piperidine, piperazine or 4-methylpiperazine.

Further preferred are compounds of formula 1 or 1A, wherein

A is —(C=O)$_a$—(CH$_2$)$_b$—O—NO$_2$; —(C=O)$_a$—(CH$_2$)$_d$—CH[(CH$_2$)$_e$—O—NO$_2$]$_2$;

—(C=O)—NR$^1$—(CH$_2$)$_b$—O—NO$_2$; —(C=O)—O—(CH$_2$)$_b$—O—NO$_2$;

—CH$_2$O—(C=O)—NR$^1$—(CH$_2$)$_b$—O—NO$_2$; —CH$_2$O—(C=O)—O—(CH$_2$)$_b$—O—NO$_2$; or

—CH$_2$O—(C=O)—(CH$_2$)$_b$—O—NO$_2$;

a is 0 or 1; b is between 1 and 6; d is 0, 1 or 2; e is 1 or 2;

R$^1$ is H, methyl or —CH$_2$O—(C=O)—NH—(CH$_2$)$_b$—O—NO$_2$; and such compounds wherein —O—NO$_2$ is replaced by

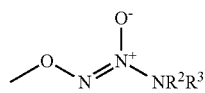

wherein R$^2$ and R$^3$ are both ethyl, or NR$^2$R$^3$ together represent pyrrolidine.

Even further preferred are compounds of formula 1, wherein
A is —(C=O)$_a$—(CH$_2$)$_b$—O—NO$_2$; —(C=O)$_a$—(CH$_2$)$_a$—CH[(CH$_2$)$_e$—O—NO$_2$]$_2$; or —CH$_2$O—(C=O)—NR$^1$—(CH$_2$)$_b$—O—NO$_2$;
a is 1; b is 2, 3, 4 or 5; d is 0 or 1; and e is 1 or 2;
R$^1$ is H or —CH$_2$O—(C=O)—NH—(CH$_2$)$_b$—O—NO$_2$; and
such compounds wherein —O—NO$_2$ is replaced by

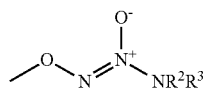

wherein NR$^2$R$^3$ together represent pyrrolidine.

Most preferred are the compounds of the Examples.

The present invention relates also to pharmaceutical compositions that comprise a compound of formula 1 or 1A as active ingredient and that can be used especially in the treatment of the diseases mentioned above. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula 1 or 1A, and at least one pharmaceutically acceptable carrier.

The invention relates also to pharmaceutical compositions for use in a method for the prophylactic or especially therapeutic management of the human or animal body, in particular in a method of treating a vascular and metabolic disease, especially those mentioned above.

The invention relates also to processes and to the use of compounds of formula 1 or 1A for the preparation of pharmaceutical preparations which comprise compounds of formula 1 or 1A as active component (active ingredient).

A pharmaceutical composition for the prophylactic or especially therapeutic management of a vascular and metabolic disease, of a warm-blooded animal, especially a human, comprising a novel compound of formula 1 or 1A as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.001 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methyl-cellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetyl-cellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy-ethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a vascular and metabolic disease, which comprises administering a compound of formula 1 or 1A, wherein the radicals and symbols have the meanings as defined above for formula 1 and 1A, in a quantity effective against said disease, to a warm-blooded animal requiring such treatment. The compounds of formula 1 or 1A can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.001 g to approximately 5 g, preferably from approximately 0.25 g to approximately 1.5 g, of a compound of the present invention.

The present invention relates especially also to the use of a compound of formula 1 or 1A, as such or in the form of a pharmaceutical formulation with at least one pharmaceutically acceptable carrier for the therapeutic and also prophylactic management of a vascular and metabolic disease, in particular of peripheral arterial disease.

The preferred dose quantity, composition, and preparation of pharmaceutical formulations (medicines) which are to be used in each case are described above.

Furthermore, the invention provides a method for the treatment of a metabolic disease, which comprises administering a compound of formula 1 or 1A, wherein the radicals and symbols have the meanings as defined above, in a quantity effective against said disease, to a warm-blooded animal requiring such treatment.

The following Examples serve to illustrate the invention without limiting the invention in its scope.

EXAMPLES

Example 1

2-{2-(6-[4-(1-Cyclohexyl-1H-tetrazol-5-yl)butoxy]-2-oxo-3,4-dihydroquinolin-1H-yl)-2-oxoethyl}-propane-1,3-diyl acetone diketal (2)

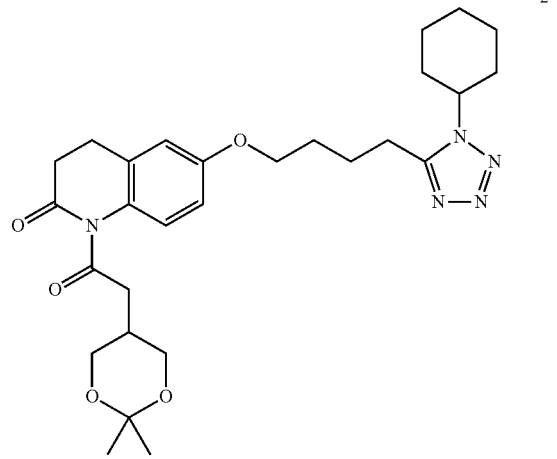

Equivalent amounts of 6-[4-(1-cyclohexyl-1H-tetrazol-5-yl)butoxy]-3,4-dihydroquinolin-2(1H)-one (cilostazol, formula 1, A=H, 554 mg, 1.5 mmol), 4-hydroxy-(3-hydroxymethyl)-butanoic acid dimethyl ketal (261 mg, 1.5 mmol), dicyclohexyl carbodiimide (DCC, 309 mg, 1.5 mmol) and 4-dimethylaminopyridine (DMAP, 183 mg, 1.5 mmol) are stirred in 5 ml $CH_2Cl_2$ for 3 days at room temperature. Dicyclohexylurea is filtered off, and the liquid evaporated and purified by chromatography (dichloromethane/diisopropylketone 97.5:2.5). The title compound 2 is obtained in 67% yield.

$^1$H-NMR (400 MHz, $CD_3OD/CDCl_3$ 9:1): δ1.27-1.58 (m, 4H), 1.40 (s, 3H), 1.41 (s, 3H), 1.72-2.06 (m, 12H), 2.28-2.37 (m, 1H), 2.66-2.71 (m, 2H), 2.84-2.89 (m, 2H), 3.01 (t, J=7.6 Hz, 2H), 3.05 (d, J=6.7 Hz, 2H), 3.71 (dd, J=7.2, 11.8 Hz, 2H), 3.99-4.07 (m, 2H), 4.31-4.40 (m, 1H), 6.78 (dd, J=2.8, 8.7, 1H), 6.82 (d, J=2.8, 1H), 7.23 (d, J=8.7, 1H).

Example 2

1-[4-Hydroxy-3-(hydroxymethyl)butanoyl]-6-[4-(1-cyclohexyl-1H-tetrazol-5-yl)butoxy]-3,4-dihydro-quinolin-2(1H)-one (3)

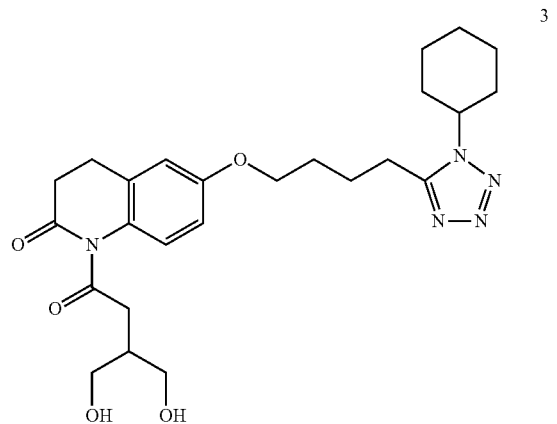 [SMILES: O=C1CCc2cc(OCCCCc3nnnn3C3CCCCC3)ccc2N1C(=O)CC(CO)CO]

A mixture of 5 mmol 2-{2-(6-[4-(1-cyclohexyl-1H-tetrazol-5-yl)butoxy]-2-oxo-3,4-dihydroquinolin-1H-yl)-2-oxoethyl}-propane-1,3-diyl acetone diketal (2, Example 1) and 0.10 g FeCl$_3$—SiO$_2$ reagent in 20 mL CHCl$_3$ is stirred at room temperature. The reaction is monitored by TLC. After completion of the ketal cleavage, the mixture is filtered, and the filtrate concentrated under reduced pressure. The product is purified by flash chromatography.

Example 3

1-[4-Bromo-3-(bromomethyl)butanoyl]-6-[4-(1-cyclohexyl-1H-tetrazol-5-yl)butoxy]-3,4-dihydroquinolin-2(1H)-one (4)

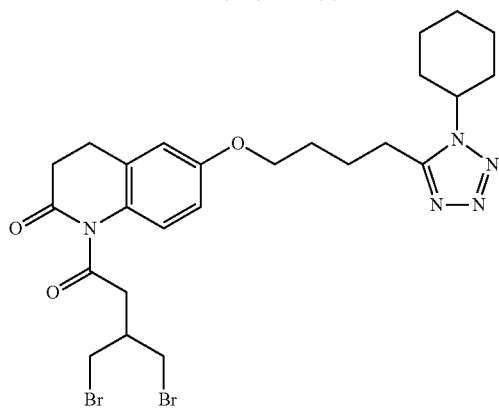

4

To a solution of 6-[4-(1-cyclohexyl-1H-tetrazol-5-yl)butoxy]-3,4-dihydroquinolin-2(1H)-one (cilostazol, 1, A=H, 2.0 g, 3.50 mmol), N,N-dimethylaminopyridine (0.043 g, 0.35 mmol) and triethylamine (0.5 ml, 0.35 mmol) in THF (100 mL) at 0° C. and under nitrogen, a solution of 4-bromo-3-(bromomethyl)butanoyl chloride (0.97 g, 3.50 mmol) in THF (5 mL) is slowly added and the reaction mixture stirred at room temperature for 2 hours. Then it is partitioned between ethyl acetate and phosphate buffer (pH=3) and extracted with ethyl acetate (3×25 mL). The organic phase is dried over Na$_2$SO$_4$ and concentrated. The crude material is purified by flash chromatography (CH$_2$Cl$_2$/acetone 7:3).

Example 4

2-{2-(6-[4-(1-Cyclohexyl-1H-tetrazol-5-yl)butoxy]-2-oxo-3,4-dihydroquinolin-1H-yl)-2-oxoethyl}-propane-1,3-diyl dinitrate (5)

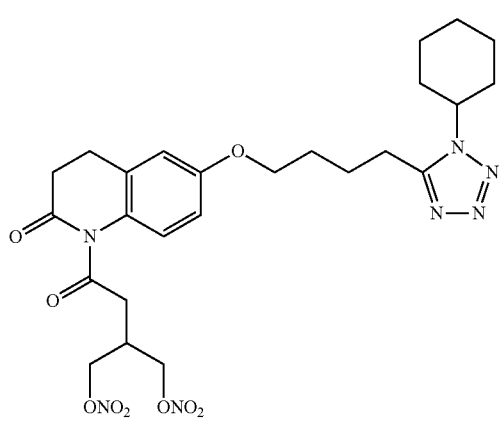

5

1-[4-Bromo-3-(bromomethyl)butanoyl]-6-[4-(1-cyclohexyl-1H-tetrazol-5-yl)butoxy]-3,4-dihydroquinolin-2(1H)-one (4, 1.5 g, 2.5 mmol, Example 3) is dissolved in CH$_3$CN (30 ml), and AgNO$_3$ (0.93 g, 5.5 mmol) is added in the dark and under nitrogen. The mixture is stirred at 85° C. for 24 hours. Then it is cooled and poured into a phosphate buffer solution (pH=3). Solid sodium chloride is added and the mixture is extracted with ethyl acetate. The organic phase is washed with phosphate buffer (pH=3, 1×25 mL), brine (3×50 mL), dried over Na$_2$SO$_4$ and concentrated. The crude material is purified by flash chromatography (CH$_2$Cl$_2$/acetone 8:2) affording crude compound, which is dissolved in H$_2$O/CH$_3$CN and freeze dried to give the desired dinitrate.

Alternatively, the compound is prepared from the corresponding diol 3 (Example 2) in the following way: 1-[4-Hydroxy-3-(hydroxymethyl)butanoyl]-6-[4-(1-cyclohexyl-1H-tetrazol-5-yl)butoxy]-3,4-dihydroquinolin-2(1H)-one (23.7 g, 0.049 mol) is added slowly to 15 g HNO$_3$ (100%, 0.24 mol) at −10° C. The resulting mixture is stirred for 10 min at 0° C., 15 g ice added to it, and stirring continued for 2 h at room temperature until brown gases (NO$_x$) disappear. The mixture is cooled to 5° C., and 2-butanol added carefully. The mixture is neutralized to pH=6 with 15.6 g NaHCO$_3$ at 0° C. After separation of the phases, the organic phase is dried with MgSO$_4$. The resulting crude mixture is purified as above to give the desired dinitrate.

Example 5

1-(4-Chlorobutanoyl)-6-[4-(1-cyclohexyl-1H-tetrazol-5-yl)butoxy]-3,4-dihydroquinolin-2(1H)-one (6)

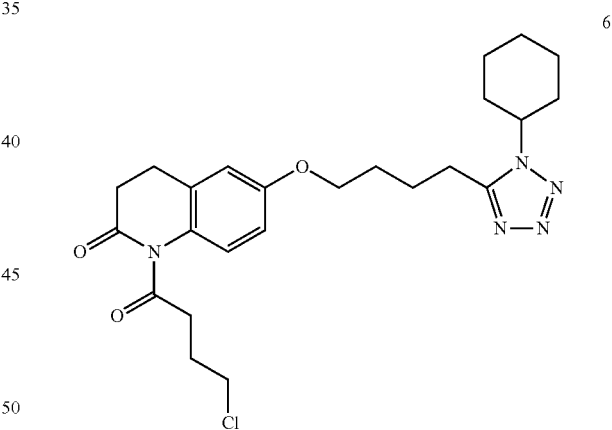

6

To a solution of 6-[4-(1-cyclohexyl-1H-tetrazol-5-yl)butoxy]-3,4-dihydroquinolin-2(1H)-one (cilostazol, 1, A=H, 15.00 g, 40.6 mmol), pyridine (6.42 g, 81.2 mmol) and 4-dimethyl-aminopyridine (DMAP, 6.45 g, 52.8 mmol) in 135 mL chloroform at room temperature is added slowly 4-chlorobutanoyl chloride (7.45 g, 52.8 mmol). The mixture is stirred at 70° C. for 20 hours. The reaction mixture is diluted with 1000 mL CH$_2$Cl$_2$, and washed with 1N HCl, saturated NaHCO$_3$ solution and brine. The organic phase is dried over sodium sulphate, and concentrated. The residue is purified by flash chromatography (silica gel, CH$_2$Cl$_2$/tert-butyl methyl ether 90:10) to give the title compound in 42% yield.

$^1$H-NMR (400 MHz, CDCl$_3$): δ1.25-1.48 (m, 3H), 1.75-1.81 (m, 1H), 1.87-2.01 (m, 1H), 2.28-2.37 (m, 10H), 2.19-2.25 (m, 2H), 2.70-2.73 (m, 2H), 2.83-2.87 (m, 2H), 2.92 (t,

J=7.6 Hz, 2H), 3.21 (t, J=7.0 Hz, 2H), 3.67 (t, J=6.4 Hz, 2H), 4.05 (d, J=6.1 Hz, 2H), 4.08-4.17 (m, 1H), 6.72 (d, J=2.9, 1H), 6.75 (dd, J=2.9, 8.8, 1H), 7.29 (d, J=8.8, 1H).

Example 6

1-(4-Nitroxybutanoyl)-6-[4-(1-cyclohexyl-1H-tetrazol-5-yl)butoxy]-3,4-dihydroquinolin-2(1H)-one (7)

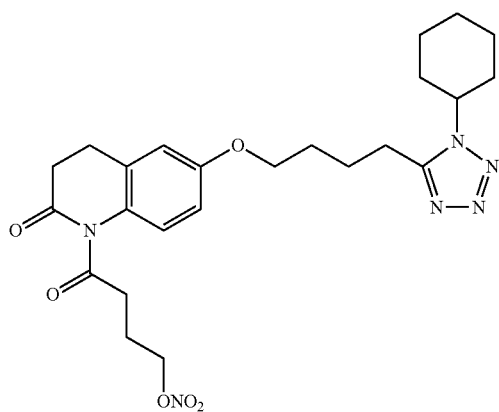

1-(4-Chlorobutanoyl)-6-[4-(1-cyclohexyl-1H-tetrazol-5-yl)butoxy]-3,4-dihydroquinolin-2(1H)-one (6, Example 5, 1.0 g, 2.1 mmol) is dissolved in CH$_3$CN (50 mL), and AgNO$_3$ (0.53 g, 3.15 mmol) is added in the dark and under nitrogen. The mixture is stirred at 75° C. for 12 hours. Then it is cooled and poured into a phosphate buffer solution (pH=3). Solid sodium chloride is added and the mixture is extracted with ethyl acetate. The organic phase is washed with phosphate buffer (pH=3, 1×25 mL), brine (3×50 mL), dried over Na$_2$SO$_4$ and concentrated. The crude material is purified by flash chromatography (CH$_2$Cl$_2$/acetone 8:2) affording the desired nitrate.

Example 7

1-{4-(6-[4-(1-Cyclohexyl-1H-tetrazol-5-yl)butoxy]-2(1H)-oxo-3,4-dihydroquinolin-1H-yl)-4-oxobut-1-yloxy}-2-pyrrolidinodiazene-2-oxide (8)

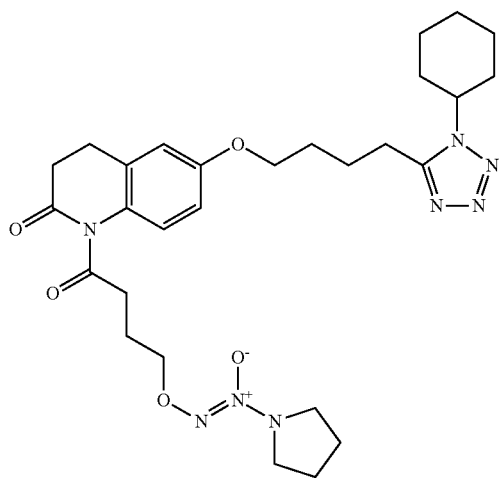

1-(4-Chlorobutanoyl)-6-[4-(1-cyclohexyl-1H-tetrazol-5-yl)butoxy)]3,4-dihydroquinolin-2(1H)-one (6, Example 5, 1.0 g, 2.1 mmol) is dissolved in CH$_3$CN (50 mL) and treated with 1.5 equivalents of sodium pyrrolidinyl diazeniumdiolate (0.48 g, 3.15 mmol). The reaction mixture is stirred for 2 days at room temperature until starting material is totally consumed as indicated by TLC. Then the mixture is concentrated and the residue is dissolved in 50 mL ethyl acetate. The organic solution is washed with water (3×50 mL) and dried over anhydrous Na$_2$SO$_4$. After removal of the solvent the crude product is purified by silica gel chromatography eluting with a solvent mixture of ethyl acetate and hexane. The product is obtained as a colorless syrup.

Example 8

1-(2-Nitroxyethylaminocarbonyloxymethyl)-6-[4-(1-cyclohexyl-1H-tetrazol-5-yl)butoxy]-3,4-dihydroquinolin-2(1H)-one (9) and 1-[N-(2-nitroxyethyl)-N-(2-nitroxyethyl-aminocarbonyloxymethyl)-aminocarbonyloxymethyl]-6-[4-(1-cyclohexyl-1H-tetrazol-5-yl)butoxy]-3,4-dihydroquinolin-2(1H)-one (10)

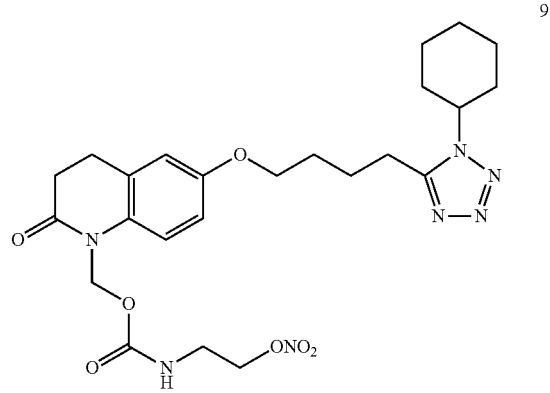

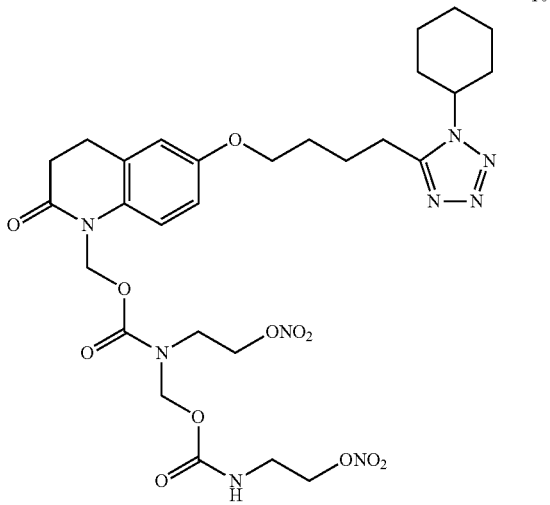

To a solution of 6-[4-(1-cyclohexyl-1H-tetrazol-5-yl)butoxy]-3,4-dihydroquinolin-2(1H)-one (cilostazol, 1, A=H, 1.00 g, 2.71 mmol) in dry THF (12 mL) NaH (60% in mineral oil, 0.217 g, 5.41 mmol) is added at room temperature under an argon atmosphere. The reaction mixture is heated to reflux for 30 min, then cooled to 0° C. A solution of chloromethyl 2-(nitroxy)ethylcarbamate (1.075 g, 5.41 mmol, obtainable from 2-nitroxy-ethyl ammonium nitrate and chloromethyl chloroformate in $CH_2Cl_2$ at 0° C. in 80% yield) in THF (1.3 mL) is added dropwise at 0° C., and the reaction mixture stirred for 1 h at room temperature. The reaction mixture is carefully quenched with water (5 mL), and THF removed on a rotary evaporator. The resulting aqueous mixture is extracted with $CH_2Cl_2$ (3×50 mL). The combined organic layers are dried ($MgSO_4$), and solvent removed under vacuum to leave a yellow oil. The crude product is purified by column chromatography (silicagel, heptanes/ethyl acetate 1:9) to give the title compound 9 in 19% yield as a colourless oil.

$^1$H NMR ($CDCl_3$): δ6.95 (d, J=10, 1H), 6.7-6.6 (m, 2H), 5.8 (br s, 2H), 5.4 (t, J=7, 1H), 4.5 (t, J=7, 2H), 4.1-4.0 (m, 1H), 3.9 (t, J=7, 2H), 3.55-3.45 (m, 2H), 2.9-2.7 (m, 4H), 2.6-2.5 (m, 2H), 2.0-1.6 (m, 11H), 1.4-1.2 (m, 3H).

$^{13}$C NMR ($CDCl_3$) δ:171.3, 155.8, 155.5, 153.9, 132.9, 128.1, 116.6, 114.9, 113.4, 72.1, 68.4, 67.9, 58.0, 38.8, 33.3, 32.2, 28.9, 25.9, 25.7, 25.2, 24.3, 23.4. LCMS: 554 (M+Na).

Compound 10 carrying two nitroxyethylaminocarbonyloxymethyl functions is obtained as a side product in 5% yield:

$^1$H NMR (broad peaks due to carbamate rotamers, $CDCl_3$): δ 6.95 (1H), 6.7-6.6 (2H), 5.8 (2H), 5.4-5.1 (3H), 4.6-4.4 (4H), 4.1-4.0 (1H), 3.9 (2H), 3.8-3.6 (2H), 3.5-3.45 (2H), 2.9-2.7 (4H), 2.6-2.5 (2H), 2.0-1.6 (11H), 1.4-1.2 (3H).

$^{13}$C NMR ($CDCl_3$): δ 171.0, 156.1, 155.5, 154.8, 153.9, 132.6, 128.0, 116.3, 114.5, 113.2, 73.2, 72.0, 70.0, 69.5, 67.7, 57.8, 45.5, 38.6, 33.1, 32.0, 28.9, 25.7, 25.5, 25.0, 24.1, 23.2. LCMS: 716 (M+Na)

The invention claimed is:

1. A compound of formula 1 wherein A is
—(C=O)$_a$—(CH$_2$)$_b$—O—NO$_2$;
—(C=O)—(CH$_2$OCH$_2$)$_c$CH$_2$—O—NO$_2$;
—(CH$_2$CH$_2$O)$_c$CH$_2$CH$_2$—O—NO$_2$; or
—(C=O)$_a$—(CH$_2$)$_d$—CH[(CH$_2$)$_e$—O—NO$_2$]$_2$;
—(C=O)—NR$^1$—(CH$_2$)$_b$—O—NO$_2$;
—(C=O)—O—(CH$_2$)$_b$—O—NO$_2$;
—CH$_2$O—(C=O)—NR$^1$—(CH$_2$)$_b$—O—NO$_2$;
—CH$_2$O—(C=O)—O—(CH$_2$)$_b$—O—NO$_2$; or
—CH$_2$O—(C=O)—(CH$_2$)$_b$—O—NO$_2$; and
a is 0 or 1;
b is between 1 and 10;
c is 1, 2 or 3;
d is 0, 1 or 2;
e is between 1 and 4; and
R$^1$ is H, C$_{1-4}$-alkyl or —CH$_2$O—(C=O)—NH—(CH$_2$)$_b$—O—NO$_2$; and such compounds wherein —O—NO$_2$ is replaced by wherein R$^2$ and R$^3$ are both ethyl or 2-aminoethyl, or NR$^2$R$^3$ together represent pyrrolidine, piperidine, piperazine or 4-methylpiperazine.

2. The compound according to claim 1 of formula 1, wherein
A is —(C=O)$_a$—(CH$_2$)$_b$—O—NO$_2$; —(C=O)—(CH$_2$OCH$_2$)$_c$CH$_2$—O—NO$_2$;
—(CH$_2$CH$_2$O)$_c$CH$_2$CH$_2$—O—NO$_2$; or —(C=O)$_a$—(CH$_2$)$_d$—CH[(CH$_2$)$_e$—O—NO$_2$]$_2$.

3. The compound according to claim 1 of formula 1, wherein
A is —(C=O)$_a$—(CH$_2$)$_b$—O—NO$_2$ or —(C=O)$_a$—(CH$_2$)$_d$—CH[(CH$_2$)$_e$—O—NO$_2$]$_2$; and
a is 0 or 1; b is between 1 and 6; d is 0, 1 or 2; and e is 1 or 2.

4. The compound according to claim 1 of formula 1, wherein
A is —(C=O)$_a$—(CH$_2$)$_b$—O—NO$_2$ or —(C=O)$_a$—(CH$_2$)$_d$—CH[(CH$_2$)$_e$—O—NO$_2$]$_2$; and
a is 1; b is 2, 3, 4 or 5; d is 0 or 1, and e is 1 or 2.

5. The compound according to claim 1 of formula 1, wherein
A is —(C=O)$_a$—(CH$_2$)$_d$—CH[(CH$_2$)$_e$—O—NO$_2$]$_2$, and
a is 1, d is 0 or 1, and e is 1 or 2.

6. The compound according to claim 1 of formula 1, wherein
A is —(C=O)$_a$—(CH$_2$)$_b$—O—NO$_2$; —(C=O)$_a$—(CH$_2$)$_d$—CH[(CH$_2$)$_e$—O—NO$_2$]$_2$;
—(C=O)—NR$^1$—(CH$_2$)$_b$—O—NO$_2$; —(C=O)—O—(CH$_2$)$_b$—O—NO$_2$;
—CH$_2$O—(C=O)—NR$^1$—(CH$_2$)$_b$—O—NO$_2$;
—CH$_2$O—(C=O)—O—(CH$_2$)$_b$—O—NO$_2$; or
—CH$_2$O—(C=O)—(CH$_2$)$_b$—O—NO$_2$;
a is 0 or 1; b is between 1 and 10; d is 0, 1 or 2; e is between 1 and 4;
R$^1$ is H, C$_{1-4}$-alkyl or —CH$_2$O—(C=O)—NH—(CH$_2$)$_b$—O—NO$_2$; and
such compounds wherein —O—NO$_2$ is replaced by wherein R$^2$ and R$^3$ are both ethyl or 2-aminoethyl, or NR$^2$R$^3$ together represent pyrrolidine, piperidine, piperazine or 4-methylpiperazine.

7. The compound according to claim 1 of formula 1, wherein
A is —(C=O)$_a$—(CH$_2$)$_b$—O—NO$_2$; —(C=O)$_a$—(CH$_2$)$_d$—CH[(CH$_2$)$_e$—O—NO$_2$]$_2$;
—(C=O)—NR$^1$—(CH$_2$)$_b$—O—NO$_2$; —(C=O)—O—(CH$_2$)$_b$—O—NO$_2$;
—CH$_2$O—(C=O)—NR$^1$—(CH$_2$)$_b$—O—NO$_2$;
—CH$_2$O—(C=O)—O—(CH$_2$)$_b$—O—NO$_2$; or —$CH_2O$—(C=O)—$(CH_2)_b$—O—$NO_2$;

a is 0 or 1; b is between 1 and 6; d is 0, 1 or 2; e is 1 or 2;

$R^1$ is H, methyl or —$CH_2O$—(C=O)—NH—$(CH_2)_b$—O—$NO_2$; and such compounds wherein —O—$NO_2$ is replaced by

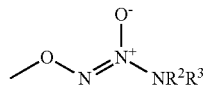

wherein $R^2$ and $R^3$ are both ethyl, or $NR^2R^3$ together represent pyrrolidine.

8. The compound according to claim 1 of formula 1, wherein

A is —$(C=O)_a$—$(CH_2)_b$—O—$NO_2$; —$(C=O)_a$—$(CH_2)_d$—CH[$(CH_2)_e$—O—$NO_2$]$_2$; or —$CH_2O$—(C=O)—$NR^1$—$(CH_2)_b$—O—$NO_2$;

a is 1; b is 2, 3, 4 or 5; d is 0 or 1; and e is 1 or 2;

$R^1$ is H or —$CH_2O$—(C=O)—NH—$(CH_2)_b$—O—$NO_2$; and such compounds wherein —O—$NO_2$ is replaced by

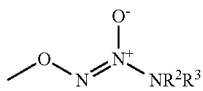

wherein $NR^2R^3$ together represent pyrrolidine.

9. The compound according to claim 1 of formula 1, wherein

A is —(C=O)—$CH_2$—CH[$CH_2$—O—$NO_2$]$_2$.

10. The compound according to claim 1 of formula 1, wherein

A is —(C=O)—$CH_2$—$CH_2$—$CH_2$—O—$NO_2$.

11. The compound according to claim 1 of formula 1, wherein

A is —$CH_2O$—(C=O)—NH—$(CH_2)_2$—O—$NO_2$.

12. The compound according to claim 1 of formula 1, wherein

A is —$CH_2O$—(C=O)—$NR^1$—$(CH_2)_2$—O—$NO_2$ and $R^1$ is —$CH_2O$—(C=O)—NH—$(CH_2)_2$—O—$NO_2$.

13. A pharmaceutical composition comprising a compound according to claim 1.

14. A compound according to claim 1 for the treatment of vascular and metabolic diseases.

* * * * *